United States Patent [19]
Morgan et al.

[11] Patent Number: 4,951,658
[45] Date of Patent: Aug. 28, 1990

[54] EYE PATCH WITH HYDROCOLLIOD ADHESIVE

[76] Inventors: Kirk M. Morgan, 6811 Mayfield Rd. #1679, Mayfield Heights, Ohio 44124; Richard E. Wyszynski, 3508 Woodridge Rd., Cleveland Heights, Ohio 44121

[21] Appl. No.: 323,117

[22] Filed: Mar. 13, 1989

Related U.S. Application Data

[63] Continuation of Ser. No. 188,412, Nov. 6, 1987, abandoned.

[51] Int. Cl.⁵ ............................................... A61F 13/12
[52] U.S. Cl. ............................................. 128/163; 2/15
[58] Field of Search ............... 128/155, 156, 163, 888, 128/889, 890, 893, 894; 2/15

[56] References Cited

U.S. PATENT DOCUMENTS

| 3,068,863 | 12/1962 | Bowman | 128/163 |
| 3,229,691 | 1/1966 | Crowe, Jr. | 128/155 |
| 3,952,735 | 4/1976 | Wirtschafter et al. | 128/163 |
| 3,972,328 | 8/1976 | Chen | 128/156 |
| 4,022,204 | 5/1977 | LeBoeuf et al. | 128/163 |
| 4,134,401 | 1/1979 | Galician | 128/163 |
| 4,331,136 | 5/1982 | Russell et al. | 128/163 |
| 4,538,603 | 9/1985 | Pawelchak et al. | 128/156 |
| 4,635,625 | 1/1987 | Teeple | 128/163 |
| 4,682,371 | 7/1987 | Heltman | 2/15 |
| 4,793,003 | 12/1988 | Riedel et al. | 128/163 X |

Primary Examiner—Randall L. Green
Assistant Examiner—Paul Prebilic
Attorney, Agent, or Firm—D. Peter Hochberg; Mark Kusner; Louis J. Weisz

[57] ABSTRACT

An eye patch (10) having a backing member with an inner periphery (22) having a hydrocolloidal adhesive for securing the patch over a person's eye and an inner fabric material for contacting the eyelid.

4 Claims, 2 Drawing Sheets

EYE PATCH WITH HYDROCOLLIOD ADHESIVE

This application is a continuation of Ser. No. 07/118,412 filed Nov. 6, 1987, now abandoned.

BACKGROUND OF THE INVENTION

This invention relates to eye patches, and in particular to occlusive patches for covering the good eye of a patient suffering from amblyopia, i.e. weak or lazy eye, for forcing the amblyopic (or bad) eye to regain full visional function.

The treatment of amblyopia by covering the good eye of a patient so as to compel the patient to use his amblyopic or bad eye is well established in ophthamology as a very effective way for treating this disorder. Amblyopia is a very common disorder among children, and despite the known effectiveness of covering the patient's good eye to correct the disorder, remains the leading cause of visual loss among children. Although the task of covering the patient's good eye would appear to be simple, in fact it has not been implemented with particularly good success. One of the obstacles to effective treatment of ambylopia remains patient and parent non-compliance with the patching process, and this non-compliance often results from problems with the patch itself.

Eye patches which are presently on the market use conventional adhesives, as are found on household adhesive tape. U.S. Pat. Nos. 4,134,401 (Galician) and 4,682,371 (Heltman) disclose eye patches having pressure sensitive adhesive strips for removably securing the patch over the user's eye, the adhesives being of the conventional contact type. U.S. Pat. No. 3,952,735 describes an eye bandage which is held in operative position by adhesive areas employing conventional adhesives. U.S. Pat. Nos. 4,331,136 (Russell et al.) and 4,635,625 (Teeple) disclose eye masks which employ adhesives for securing the device to the person's face, and these too use conventional adhesives. Thus, such conventional adhesive system have been in wide use for many years on eye patches and the like despite their well-known disadvantages; namely, tissue trauma upon removal of the adhesive device, allergic reaction to adhesive materials, the build-up of sweat under the patch which causes skin rash at the interface of the adhesive and the skin, and the ultimate failure of the adhesive, which causes the patch to fall off. Indeed, parents often report that during the summer when patching of their children's eyes would be expected to be most successful, they have to repeatedly re-apply the patch to the child. Once tissue rash or breakdown occurs, the options available to the physician for treating amblyopia become very limited, and patient frustration leads to non-compliance of the patching process and the failure of treatment of the ailment.

In view of these well-known shortcomings of the conventional adhesive systems used on eye patches, alternate patching techniques have been tried. For example, black felt patches with elastic bands ("the pirate patch") is sometimes used, but this is quite ineffective because of the ease with which the child can move the path to one side so that he can use his good eye to see around the patch. In the common situation where the child wears glasses, it is a known technique to apply tape to the lens of the glasses over the good eye, or to apply a commercial product known as the Lindener occluder to force the child to use the bad or amblyopic eye to see with. Alternatively, a technique is known whereby the lens of the good eye is reduced by a correction in the lens over that eye. However, these modifications to eye glasses are not effective because the child frequently turns his head to one side to enable him to use his good eye to see around the glasses' frame. It has been proposed to use opaque contact lenses, but this technique also has been ineffective. Indeed, one ophthamologist actually placed the cast around the head of the child to cover the good eye, only to find out later that this child could see around the cast.

Thus, even though the technique of covering the good eye of an amblyopic patient is known to be very effective in treating amblyopia, there has heretofore not been available any effective means for covering the good eye of the patient for prolonged periods to enable the patient to enjoy the benefits of this simple technique.

As discussed below, the present invention makes use of hydrocolloidal materials in conjunction with an adhesive in order to provide an eye patch which remains in place over a patient's eye. The present invention does not reside in the discovery of such hydrocolloidal materials, indeed, hydrocolloidal dressing materials have been used successfully for many years by general surgeons and internists to cover burns, pressure sores and wounds. For example, U.S. Pat. No. 3,972,328, issued Aug. 3, 1976 to J. L. Chen, discloses a medical wound dressing comprising a semi-open cell polymeric flexible foam having attached to one side a water impervious flexible polymeric film and to the other side a pressure sensitive adhesive composition. The adhesive is prepared by forming a mixture of a hydrocolloid, a rubbery elastomer, a tackifier and plasticizer. The presence of the hydrocolloid in the adhesive layer provides a material for absorbing moisture such as perspiration and wound exudate, and for transferring such moisture from the surface of the skin to the layer of the open-cell foam where it can evaporate through sides of the bandage. The foregoing Chen patent refers in turn to the following patents directed to medical dressings for removing liquid: U.S. Pat. Nos. 3,339,546, 3,122,140, 3,122,141, 3,122,142, and 3,156,242. A more recent patent disclosing another occlusive dressing having an adhesive layer with a homogeneous blend of one or more pressure sensitive adhesive materials and one or more water dispersable hydrocolloidal materials is U.S. Pat. No. 4,538,603. This patent refers to the previously cited patent to Chen, and further refers to British Patent No. 2,061,732, and U.S. Pat. Nos. 4,192,785, and 3,339,546 for disclosures of materials incorporating hydrocolloids. It is significant that all these patents which relate to any type of bandages relate to devices for covering various sorts of wounds. None of them have anything to do with covering any portion of the skin which has not been subjected to some sort of trauma which the bandage is to protect or be used in the treatment thereof. A commercial version of such wound dressing is sold under the name "DuoDERM," and is specifically stated as being used for use on small burn areas. The patents cited above are all incorporated herein by reference. As widespread as the use of wound dressings having hydrocolloidal materials used in conjunction with adhesives is, it has not heretofore occurred to ophthalomogists to apply the foregoing material to patches used for treating amblyopia. Neither internists, surgeons, and opthalomogists nor the companies that market wound dressings having hydrocolloidal materials, appear to have ever considered using such materials for occlusional therapy.

SUMMARY OF THE INVENTION

It is an object of the present invention to provide an improved eye patch.

Another object of the present invention is to provide an improved eye patch for the treatment of ambylopia.

Yet an additional object of the present invention is to provide an eye patch which can be adhered over a patient's eye without the rapid loss of adhesive strength due to moisture as characterized in presently known eye patch adhesives.

A further object is the provision of an eye patch to be adhered over a patient's eye, which does not cause trauma to the skin upon the removal of the patch.

Still a further object of the present invention is to provide an improved eye patch which can be adhered to the skin of a patient over the patient's eye, which does not accumulate sweat or other moisture which would tend to cause skin rash and loss of adhesive strength as occurs in known eye patches which employ adhesives.

A general object is to provide an eye patch which can be made using known materials and manufacturing techniques, and which is effective in use. Other objects will appear from the description to follow and from the appended claims.

DETAILED DESCRIPTION OF THE PREFERRED EMBODIMENT

Figure 1:
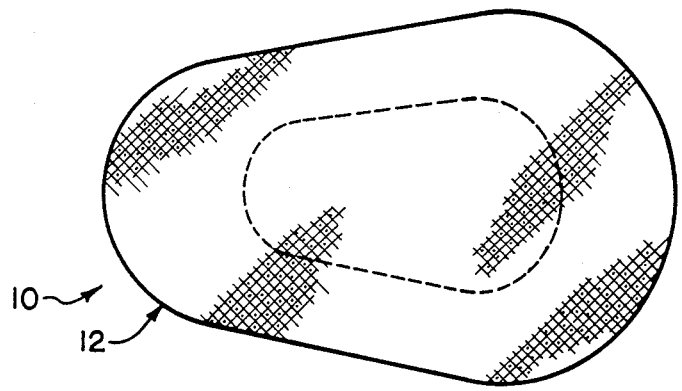
FIG. 1 is a plan view of an eye patch according to the invention.
Figure 2:
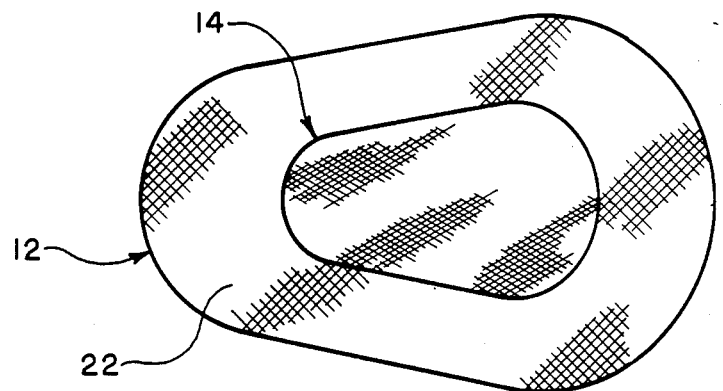
FIG. 2 is a bottom elevation of the eye patch shown in FIG. 1.
Figure 3:
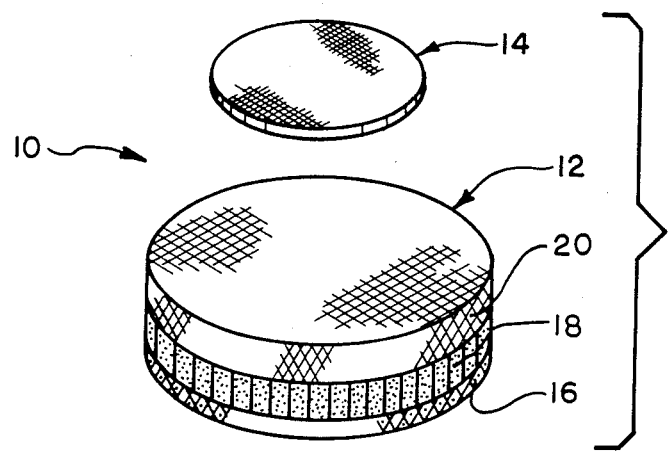
FIG. 3 is a diagrammatic view of an eye patch according to the present invention, shown in exploded form.
Figure 4:
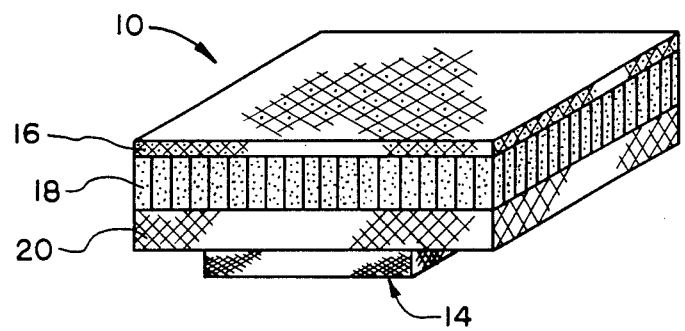
FIG. 4 is a perspective view of a portion of an eye patch according to the invention.
Figure 5:
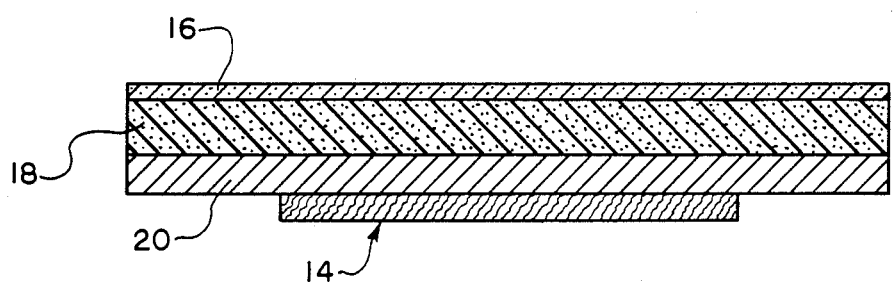
FIG. 5 is a cross-sectional view of an eye patch according to the invention.

Referring to the drawings, an eye patch 10 according to the preferred form of the invention is shown. The eye patch has a backing or outer member 12 and an inner member 14 (as used herein, the term "inner" refers to a layer or member which is closest to the eye when the eye patch is applied to a patient, and the term "outer" refers to layers or members which are spaced relatively further from the eye than an "inner" member or layer). Outer member 12 is preferably made from the product marketed by E. R. Squibb & Sons, Inc. under the brand name "DuoDERM," and is of the type disclosed in U.S. Pat. Nos. 4,538,603 and 3,972,328 cited previously. Thus, backing member 12 includes a polymeric film or skin 16, a semi-open cell elastic or flexible foam intermediate layer 18, and an inner layer 20 which is preferably a homogeneous blend of one or more pressure sensitive adhesive materials and one or more dispersable hydrocolloidal materials. Adhesive layer 20 can be composed of more than one adhesive layer, having appropriate blends of adhesive materials, hydrocolloidal materials for dispersing water, a tackifier, a plasticizer and/or solvent. One or more water swellable cohesive strengthening agents and/or one or more natural or synthetic polymers for developing elastomeric properties when hydrated can be included with the hydrocolloidal materials. References made to the DuoDERM product and to the patents cited above which describe the foregoing product, for a more complete description of backing member 12.

Inner member 14 is secured to the adhesive inner face of backing member 12. Inner member 14 is preferably a piece of black felt which is configured and dimensioned so that it can be placed generally concentrically within the edges of backing member 12 so that a peripheral portion 22 of adhesive is exposed which can be attached to the skin surrounding the patient's eye. Inner member 14 is provided for protecting the lid of the eye of the patient. If for some reason the backing member were not opaque, it would be important that inner member 14 be opaque.

Backing member 12, and peripheral portion 22 are preferably shaped to conform to a person's eye socket to facilitate application of the patch to the socket and over the eye. Inner member 14 can be similarly shaped. A patch 10 for use on a child would typically have a length of about 2.5 inches and a width (at its widest portion) of about 2.0 inches. Eye patch 10 would preferably be packaged in a sealed paper and/or plastic envelope, and the adhesive portion could be secured to a transfer member so that the transfer paper could be peeled off the adhesive and the eye patch applied to the user's eye. Application of the eye patch is the same as in prior adhesive eye patches, in that the patient simply places the patch over the eye and presses the peripheral portion against the skin around the eye socket to adhere the eye patch over the eye. The presence of the hydrocolloidal material with the pressure sensitive adhesive assures that the patch can remain in place for an extended period, without the adhesive bond being so weakened by sweat or other moisture that it could only hold the patch in place for the short period of time in which the adhesives of known patches are effective. Furthermore, the hydrocolloidal material draws moisture away from the interface between the adhesive and the skin, avoiding the problems of skin rashes and trauma to the skin upon removal of the patch, as occurred in the prior art.

Tests have shown that patches according to the invention can be worn for periods as long a week at a time, without falling off, even when worn under sweaty or humid conditions, and without causing allergic reactions or skin trauma.

Tests of eye patches according to the preferred embodiment of the invention have proven very successful. Two case studies are set forth below:

CASE NUMBER 1

WJR was a six year old white male who was followed by the Eye Clinic at Cleveland Metropolitan General Hospital, Cleveland, Ohio for exotropia of 25 prism diopters associated with a dense amblyopia of the right eye. The amblyopia was treated with limited success during the spring months but became refractory during the hot summer months. The mother stated tht the patches would regularly "fall off" the patient.

Several patches were fashioned using hydrocolloidal dressings according to the invention and given to the mother with instructions to allow the patches to remain over the left eye for as many days as possible up to a period of a week before changing. The patient and parent returned six weeks later and reported that the patient tolerated each patch for a period of five to seven days. Additionally, the parent volunteered the information that at about one week after being worn the patch would spontaneously fall off, often to be found in the patient's bed in the morning.

The patient's ambyopia resolved to a great extent and required only four additional weeks of patching to obtain equal vision and alternating fixation.

CASE NUMBER 2

JHL, a seemingly immature 7 year old white male with longstanding esotropia and moderately dense amblyopia of the left eye, was seen in the Eye Clinic at University Hospitals of Cleveland, Ohio. The chart and patient's mother revealed a multitude of failed attempts at occlusional patching primarily because the patient would repeatedly remove the patches soon after they were applied. The patient verbalized an uncomfortable feeling when patched.

The patient and mother agreed to try the hydrocolloidal dressing patch. The patient returned five weeks later and his mother reported much improved (although not perfect) compliance with occlusional patching. The patient noted increased comfort. The amblyopia had partially resolved and the patient was instructed to wear the patch for an additional 6 weeks before returning.

As noted previously, fabrication of eye patches according to the invention can be accomplished using known materials and manufacturing techniques. The hydrocolloidal materials are presently commercially available, the backing member and felt inner member are commercially available, and the method of securing the patch to the adhesive on the backing member is known. The present invention thus provides a significantly improved and highly effective eye patch for treating ambylopia and for protecting the eye.

The invention has been described in detail with particular emphasis on the preferred embodiment thereof. However, it should be understood that variations and modifications within the spirit and scope of invention may occur to those skilled in the art to which the invention pertains.

We claim:

1. An eye patch for covering an individual's eye comprising:
    a backing member, and
    an inner member,
    wherein said backing member includes a layer of polymeric foam, and a pressure sensitive hydrocolloidal adhesive, said backing member being dimensioned to engage an individual's skin surrounding the eye, and wherein said inner member is made of a fabric like material which is attached to said adhesive inwardly of the periphery of said backing member, said inner member being dimensioned to protect an individual's eyelid, and wherein further, a portion of said eye patch disposed over the individual's eyelid is substantially opaque.

2. The invention of claim 1 wherein said hydrocolloidal adhesive comprises a blend of pressure sensitive adhesive material and a water dispersable hydrocolloidal material.

3. The invention of claim 1 wherein said backing member is shaped to conform to the shape of an eye socket.

4. The eye patch according to claim 1 wherein the periphery of the backing member is shaped to conform to the shape of an eye socket for facilitating adhesion of the adhesive to the skin on the socket.

* * * * *